United States Patent
Becker et al.

(10) Patent No.: US 6,305,907 B1
(45) Date of Patent: Oct. 23, 2001

(54) PROCESS FOR EVACUATING A WET GAS A TREATMENT DEVICE TO CARRY OUT THIS PROCESS AND A SUCTION PUMP FOR A TREATMENT DEVICE OF THIS TYPE

(75) Inventors: Erich Becker, Bad Krozingen; Heinz Riedlinger, Bremen, both of (DE)

(73) Assignee: KNF Neuberger GmbH, Freiburg (DE)

( * ) Notice: Subject to any disclaimer, the term of this patent is extended or adjusted under 35 U.S.C. 154(b) by 0 days.

(21) Appl. No.: 09/455,121

(22) Filed: Dec. 6, 1999

Related U.S. Application Data

(63) Continuation of application No. PCT/EP98/04509, filed on Jul. 3, 1998.

(30) Foreign Application Priority Data

Jul. 30, 1997 (DE) .............................................. 197 32 808

(51) Int. Cl.$^7$ .................................................. F04B 49/00
(52) U.S. Cl. .......................... 417/53; 417/243; 417/201
(58) Field of Search ............................. 417/53, 201, 243, 417/373, 298, 440, 413.1; 137/512.15, 854, 855, 856

(56) References Cited

U.S. PATENT DOCUMENTS

| | | |
|---|---|---|
| 3,027,651 | 4/1962 | Nerge . |
| 4,113,410 | 9/1978 | Ando . |
| 4,580,604 * | 4/1986 | Kawaguchi et al. .................. 137/856 |
| 5,275,541 * | 1/1994 | Becker et al. ......................... 417/413 |
| 5,295,791 * | 3/1994 | Meise ...................................... 417/52 |
| 5,421,368 * | 6/1995 | Maalof et al. ......................... 137/856 |
| 5,509,790 * | 4/1996 | Shuderi et al. ........................ 417/201 |

FOREIGN PATENT DOCUMENTS

| | | |
|---|---|---|
| 945 286 | 7/1956 | (DE) . |
| 26 07 640 A1 | 9/1976 | (DE) . |
| 37 10 782 A1 | 10/1988 | (DE) . |
| 44 45 054 A1 | 6/1996 | (DE) . |
| WO 96/12557 | 5/1996 | (WO) . |

\* cited by examiner

*Primary Examiner*—Charles G. Freay
(74) *Attorney, Agent, or Firm*—Akin, Gump, Strauss, Hauer & Feld, L.L.P.

(57) ABSTRACT

A process for evacuating a wet or liquid conveying medium out of the treatment chamber (2) of a treatment device (1) using a pumping device (3) that has a single or multi-stage suction pump (4) is provided, where the conveying medium is cooled off during the evacuation along the flow path such that the conveying medium in the pumping device (3) is in the liquid aggregate state or is converted into that state. A treatment device for carrying out the process as well as a single or multi-stage suction pump for this treatment device is also provided. In order to prevent a re-vaporization of the condensate or condensate film remaining in the suction pump (4), it is provided in the process and associated treatment device (1) that the cooling of the conveying medium is done at least in the area of at least one pump head (7) of the suction pump (4) and/or one connection channel connecting subsequent pump stages of the multi-stage suction pump to each other, and that at least one pump head (7) and/or the connection channel is cooled off below the vaporization temperature or boiling temperature present at the given evacuation pressure.

14 Claims, 3 Drawing Sheets

PROCESS FOR EVACUATING A WET GAS A TREATMENT DEVICE TO CARRY OUT THIS PROCESS AND A SUCTION PUMP FOR A TREATMENT DEVICE OF THIS TYPE

CROSS REFERENCE TO RELATED APPLICATIONS

This application is a continuation of International Application No. PCT/EP98/04509, filed Jul. 3, 1998.

BACKGROUND OF THE INVENTION

The invention involves a process for evacuating a wet or liquid conveying medium out of the treatment chamber of a treatment device using a pumping device that has a single or multi-stage suction pump, where the conveying medium is cooled during the evacuation along the flow path such that the conveying medium in the pumping device is in the liquid aggregate state or is converted into that state.

The invention also involves a treatment device for carrying out the above-named process, having a treatment chamber, which is connected to a pumping device for evacuation, and a single or multi-stage suction pump, which is provided for the pumping device, where the pumping device can be cooled at least in a partial area using at least one cooling device such that the conveying medium in the pumping device is found in the liquid aggregate state or is converted into that state.

Furthermore, the invention also contains a single or multi-stage suction pump, especially for the treatment device described above, having at least one intake valve that is located in a pump head and at least one outlet valve, where at least one of these valves has a valve disc that is controlled by the conveying medium and which in the closed position of the valve fits so that it seals on a valve sealing surface of the pump head, which encloses at least one valve opening.

Treatment devices of this type are known for or example, as autoclaves for sterilizing medical items for daily use. These previously known treatment devices have an airtight sealable treatment chamber in which the instruments located therein are exposed prior to sterilization at first to a so-called fractionated pre-vacuum, in which through repeated evacuation of the air in exchange with the periodic incoming flow of steam, an especially good air removal out of the narrow-lumen instruments can also be achieved. During the sterilization operation, the instruments are exposed in the treatment or sterilization chamber to hot water vapor under partial vacuum. In order to quickly dry the instruments after sterilization so that there are no residues, a so-called post-vacuum is in turn created subsequently in the treatment chamber, which shortens the drying times of the sterilizing item and should optimize the drying operation.

For the evacuation, the sterilization chamber of these types of previously known steam sterilization devices is connected to a pumping device, which has a vacuum pump. Due to the impingement of the vacuum pump with water steam, thus far, only water ring pumps or diaphragm pumps have been used. Due to the structural dimensions and the disadvantages of a water ring pump, the smaller steam sterilization devices provided for a doctor's office, for example, usually utilize only diaphragm pumps.

For this reason, a treatment device constructed as a steam sterilizer, of the type noted above, has already been created. It has a pumping mechanism for the evacuation of the treatment or sterilization chamber, which utilizes a suction pump operated in a manner free from water, such that in the suction line provided between the treatment chamber and the suction pump, a water free cooled condenser is connected intermediately in order to convert the conveying medium flowing through the suction line of the pumping device into the liquid aggregate state. (See German Patent DE 44 45 054 C2).

In German Patent DE 44 45 054 C2, it is also described how the treatment chamber of the previously known processing device can be evacuated by opening a solenoid valve and switching on the suction pump at a predetermined pressure at the program start. Then, the solenoid valve is closed and steam is conducted from a steam generator into the pressure chamber until a preset excess pressure is reached. By again opening the solenoid valve and switching on the diaphragm pump, the steam/air mixture is in turn suctioned off to achieve a defined partial vacuum, such that the water vapor coming out of the treatment chamber condenses in a cooling device constructed as a condenser and is collected in a condenser collecting vessel so that the diaphragm pump of the previously known treatment device only pumps air.

In coupling a conventional diaphragm vacuum pump with a conventional autoclave, however, the following problem occurs: After the end of a sterilization operation, the steam is expelled through the vacuum pump via a connection line. In the cold connection line and the cold vacuum pump, at least a part of the steam condenses. This condensate is pumped off by the vacuum pump. It is a problem in this that during the operation in the area of the pump head that is heating up, a re-vaporization of the condensate can occur, so that then a correspondingly larger volume must be pumped off. This takes a considerable amount of time.

A re-vaporization of this type is also not ruled out by the fact that in the suction line provided between the treatment chamber and the suction pump, a condenser is intermediately connected. The problems caused by a re-vaporization of this type also occur, in addition to the autoclaves named at the beginning, for all other types, for example, in treatment devices used for gel drying, out of the processing chamber of which a wet or liquid conveying medium is to be evacuated. Here, a wet conveying medium is understood to be, for example, any gas or gas mixture which transports at least a partial quantity of a substance found in the form of a gas or vapor state or a drippable liquid state.

SUMMARY OF THE INVENTION

The object of the invention is thus to create a process as well as a treatment device of the above-noted type, which allows a rapid and effective pumping out of a wet conveying medium of this type.

In the process of the above-noted type, the solution according to the invention resides especially in that the cooling of the conveying medium is done at least in the area of at least one pump head of the suction pump and/or one connection channel that connects together two pump stages of a multi-stage suction pump, which follow each other in the flow direction, and that the at least one pump head and/or the connection channel of the suction pump is cooled off below the vaporizing or boiling temperature present at the given evacuation pressure.

In the treatment device of the above-noted type, the solution according to the invention resides in particular in that at least one cooling device is provided for cooling at least one of the pump heads of the suction pump and/or one connection channel that connects together two pump stages of a multi-stage suction pump, which follow each other in the flow direction, and that the pump head and/or the connection channel of the suction pump is cooled off using this cooling device in such a manner that the head temperature of the suction pump and/or the inner temperature of the connection channel is cooled off below the vaporizing or boiling temperature present at the given evacuation pressure.

In the objects of the invention described above, the suction pump pulls the wet and, for example, steam-containing conveying medium out of the treatment chamber, such that the steam conducted along with it is compressed when it is moved out in the suction pump at atmospheric pressure and condenses at head temperatures below 100° C. in the pump. This condensate is pumped via the suction pump into the open. In the dead spaces or in the connection line connecting the two adjacent pump stages to each other, however, a residue of the condensate can be left over. Upon a suction stroke, the pressure in the operating space in the suction pump is reduced. At least a part of the condensate that stays in the suction pump could then vaporize if the suction pressure in the vacuum pump were to fall below the vaporizaton pressure corresponding to the head temperature in the pump head at that moment. Such a revaporization of the condensate found in the pump head would, however, lead again to an enlargement of the pumping volume to be pumped off and thus to a reduction of the suction volume as well as the suction output of the vacuum pump. In order to rule out such a re-vaporization, it is provided in the process according to the invention that the cooling of the conveying medium is done at least in the area of at least one pump head and/or a connection channel of the single or multi-stage suction pump connecting adjacent pump stages to each other. In this manner, the at least one pump head and/or the connection channel of the suction pump is cooled off below the vaporization temperature or boiling temperature present at the given evacuation pressure. Since in this way the condensate pumped through the at least one pump head and/or the connection channel never can reach the desired vaporization pressure in the treatment chamber that corresponds to the boiling temperature, a re-vaporization of the condensate or condensate film found in the pump head or in the connection channel is ruled out with certainty.

In order to cool the at least one pump head and/or the connection channel provided between the pump stages of a multi-stage suction pump, Peltier elements or any other suitable cooling device can be used. An especially simple and advantageous embodiment according to the invention provides, however, that the cooling device is constructed as air cooling, and preferably as fan cooling.

However, it is especially advantageous, when the pump head arranged in the cooling stream of an air cooling device and/or the connection channel of the suction pump have/has cooling ribs on the outside in order to enlarge the cooling surface and if necessary for flow conductance of the cooling stream. In this embodiment, the conveying medium can condense in the area of the pump head and/or the connection channel or be kept in the liquid aggregate state without a greater manufacturing and construction expense being necessary. In this way, the cooling of the pump head or connection channel also at the same time provides for a cool running of the pump, which favors a long lifetime of the pump and long service intervals.

As is known, water in the liquid state has a considerably smaller volume than in the vapor state. If in the closed system between the treatment chamber and the pumping device, the water vapor generated during a process operation is cooled off and condensed in the area of the pumping device using a cooling device, then at the same time, the volume of the original vapor conveying medium is reduced to a fraction of the volume during the condensation. By this reduction in volume in the area of the pumping device, a condensation pump effect occurs, which defines or at least supports the pumping capacity of the pumping device. In order to be able to use this condensation pump effect as completely as possible for evacuation of the treatment chamber, it is advantageous when in the flow passage provided between the treatment chamber and the outlet of the pumping device, a non-return valve is intermediately connected.

In this way, a preferred embodiment is provided in which the suction pump is constructed as a single or multi-stage diaphragm pump and in which the nonreturn valve is preferably the outlet valve of the diaphragm pump or one of its pump stages cooled in the area of the pump head. A diaphragm pump of this type can not only be constructed in a small, compact and condensate-insensitive manner, but also readily has the required non-return valve at the pump outlet, depending on the structure.

A preferred embodiment according to the invention provides that the treatment device is constructed as a vapor sterilization device and its treatment chamber is constructed as a sterilization chamber.

Using the object of the invention described at the beginning, a revaporization of the condensate or condensate film found :in the at least one pump head is prevented. In order to then be able to lead away the liquid conveying medium present in the valve spaces or in the condensing space, the pump must be designed so that it can, for example, automatically empty by gravity and/or because of its pumping action. When using a pump which has at least one valve with a valve disc controlled by the conveying medium, however, small liquid quantities of, for example, one or two drops can readily cause the valve disc to become "adhered" to the valve seat and cause small differential pressures corresponding at low absolute pressures to become insufficient in order to move the valve disc. So that adhering effects of this type are avoided, according to another proposal in accordance with the invention, the sealing contact positions between the sealing side of the valve disc and the sealing surface of the pump head surrounding the valve opening are constructed essentially as linear contact positions. By these linear contact positions a planar support of the valve disc is prevented, which otherwise could lead to undesired adhering effects and—for small differential pressures—to corresponding disturbance at the valve.

In order to prevent these adhering effects if necessary also on the side that faces away from the sealing side of the valve disc, it is advantageous when the contact positions are formed between, on the one side, the rear side of the valve disc, which faces away from the sealing side, and on the other side, a support for the valve disc located in the open position, essentially as point-shaped and/or also as linear contact positions.

It is advantageous when the sealing surface has in the pump head and/or the sealing side of the valve disc, at least one ring projection with preferably a cross section that tapers conically to the contact position and surrounds a valve opening. However, an embodiment is preferred which has on the sealing surface of the pump head at least a conical ring projection.

In order to prevent these adhering effects also on the rear side of the valve disc that faces away from the sealing side, it is advantageous when the rear-side support for the valve disc located in the open position and/or the valve disc rear side has a profiling as linear and/or point-shaped contact positions for reducing the support surface.

In this way, the rear-side support for the valve disc can be constructed through the edges of a stepped projection or several stepped projections having preferably linear contact positions. It is advantageous when the suction pump is manufactured in its areas impinged by the conveying medium out of corrosion-resistant materials. In this way, a long lifetime of the pump as well as long service intervals are even more favored.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
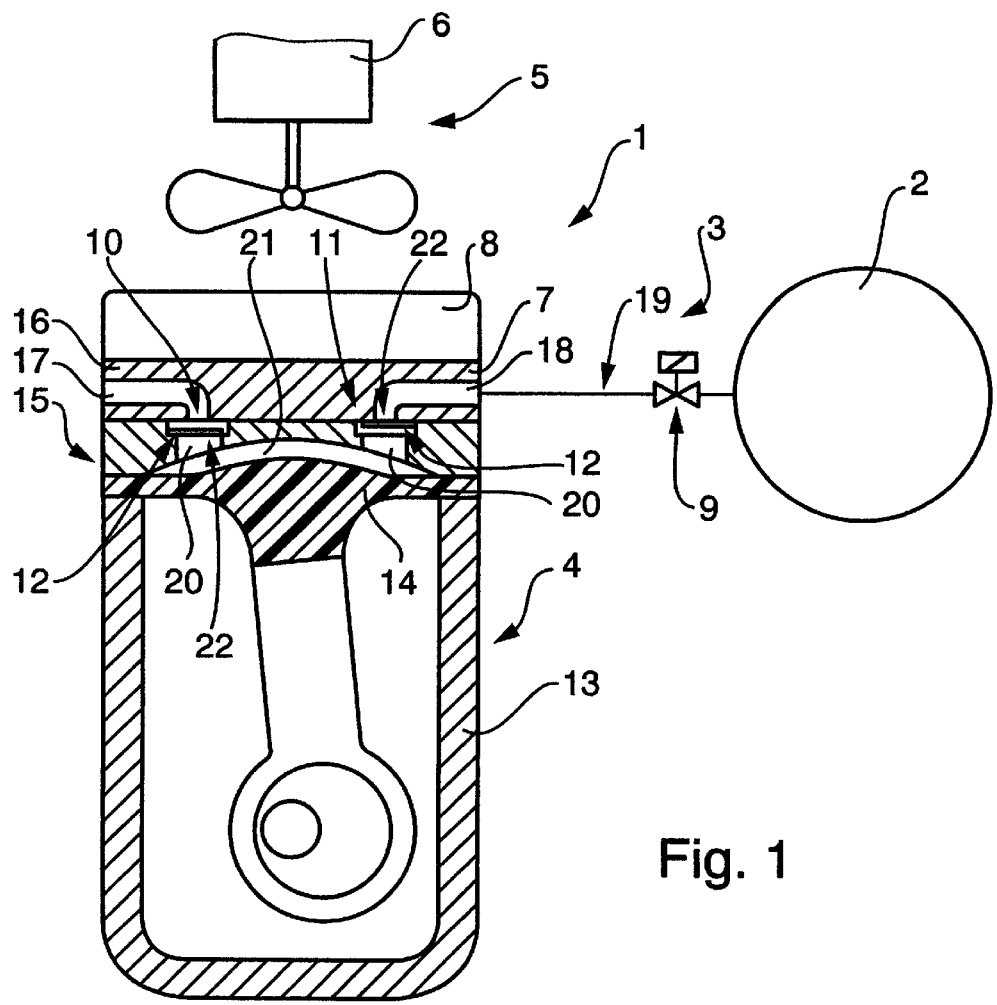
FIG. 1 is a schematically depicted treatment device in accordance with the present invention, constructed here as a steam sterilization device with a treatment or sterilization chamber which is connected to a pumping device which has a vacuum pump for evacuating the treatment or sterilization chamber.

In FIG. 1, a treatment device constructed as a vapor sterilization device 1 is depicted which has an airtight sealable treatment and sterilization chamber 2. Onto the sterilization chamber 2, a pumping device 3 is connected which functions for evacuating the sterilization chamber 2. This pumping device 3 has a suction pump 4 constructed here as a diaphragm pump, which can pump condensate as well as generate a vacuum.

The pumping device 3 can be cooled in a partial area using a cooling device 5, such that the conveying medium of the pumping device 3 is in the liquid aggregate state or is converted into this state.

As shown in FIG. 1, the cooling device 5 has a cooling fan 6. The pump head 7 of the suction pump 4 arranged in the cooling stream of the cooling fan 6 has cooling ribs 8 on the outside for cooling surface enlargement as well as for flow conductance of the cooling stream.

After the instruments to be sterilized and other medical items for daily use have been placed in the airtight sealable sterilization chamber 2, the sterilization chamber 2 is evacuated to 200 millibar, for example. The-reafter, if necessary, through repeated evacuation of the air located in the sterilization chamber 2, an especially good air removal can also be achieved out of narrow lumen instruments and the like in the exchange with the periodic incoming flow of steam.

For the subsequent sterilization process, the preferably electrically activated closing valve 9 located between the sterilization chamber 2 and the vacuum pump 4, is closed in the stream conduit in order to heat up the sterilization chamber 2 and fill it with steam under excess pressure.

After the termination of this cycle, a post-vacuum is created in the sterilization chamber 2, so that the water that has possibly condensed on the instruments and the like is evaporated, and the sterilization item can become completely dry. To do this, the closing valve 9 is at first opened and the steam flows out via the suction pump 4 as long as additional excess pressure is prevalent in the sterilization chamber 2. In this manner, at least a part of the vapor condenses in the suction pump 4 and is pumped in liquid form into the open.

When the excess pressure in the sterilization chamber 2 is taken away, the outlet valve 10 of the diaphragm pump also closes in the rhythm of the pump operation as a non-return valve. The suction pump 4 then pulls the steam-containing conveying medium out of the sterilization chamber 2 so that the steam that is conducted along with it is compressed when it is moved out of the suction pump 4 into the atmospheric pressure and condenses in the pump at head temperatures below 100° C. The condensate is pumped via the suction pump 4 into the open. In the dead spaces, however, an additional residue of the condensate can remain.

During the suction stroke, the pressure in the operating space of the suction pump 4 is reduced. At least a part of the condensate remaining in the suction pump 4 could then vaporize if the suction pressure in the vacuum pump 4 were to fall below the vaporization pressure corresponding to the momentary head temperature at the pump head 7 according to FIG. 2. Such a re-vaporization of the condensate or condensate film found in the pump head 7 would, however, lead again to an increase in the pumping volume to be pumped out and thus to a reduction of the suction volume as well as suction capacity of the vacuum pump 4.

In order to rule out such a re-vaporization, the pump head 7 of the vacuum pump can be cooled using the cooling device 5, such that the head temperature lies approximately in or preferably below the vaporization or boiling temperature, which corresponds to the desired vaporization pressure in the sterilization chamber 2 in this sterilization process.

Figure 2:
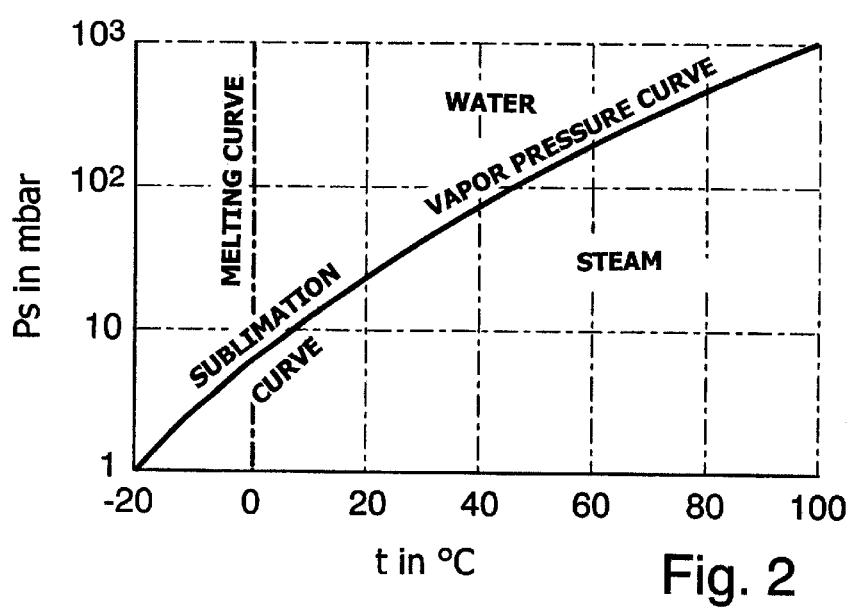
FIG. 2 is the vapor pressure curve of water, which shows the boiling temperature (abscissa—x-axis) as function of the vapor pressure (ordinate—y-axis)

Should, for example, during the post-vacuum in the sterilization chamber 2 a vaporization pressure of 200 millibar be reached, then it can be gathered from the customary water steam table or from the vapor pressure curve of water depicted in FIG. 2, that a vaporization pressure of this type corresponds to a vaporization and boiling temperature of 60.09° C. In order to rule out a re-vaporization of the condensate or condensate film located in the pump head 7 with certainty, the cooling device 5 is designed having a cooling fan 6 that is capable of a corresponding output, for example, and/or by a corresponding design of the cooling ribs 8 provided on the pump head 7, such that the pump head 7 is cooled during this sterilization process to below 60.09° C. Since in this way condensate pumped through the pump head never can reach the boiling temperature corresponding to the desired vaporization pressure in the sterilization chamber 2, a re-vaporization of the condensate or condensate film located in the pump head 7 is ruled out with certainty.

In the steam sterilization device 1 depicted here, the sterilization chamber 2 can be quickly and effectively evacuated.

Since the steam-containing conveying medium of the pumping device 3 is cooled using the cooling device 5, and the steam can thus condense, and since the volume of the condensate amounts to a fraction of the original water vapor volume, the pumping volume to be pumped out is clearly reduced. At the same time, in the closed system between the sterilization chamber 2 and the outlet valve 10 of the suction pump 4, a condensation pump effect occurs, which additionally supports the pumping capacity of the pumping device 3.

Since the cooling device 5 is designed so that the condensate located in the pump head 7 never reaches the boiling temperature corresponding to the vapor pressure desired in the sterilization chamber 2, an undesired and capacity reducing re-vaporization of the condensate or condensate film located in the pump head 7 is prevented with certainty. At the same time, by the cooling of the vacuum pump 4 in the area of the pump head 7, a cool running of pump is caused which favors a long lifetime of the vacuum pump 4 and long service intervals. The cooling device 5 can, for example, be operated in the form of an air cooling as an uncontrolled cooling system. Since in an air cooling of this type, only the cooling fan 6 is to be operated, the energy consumption of the cooling device 5 can be kept small. In this manner, the condensate accumulating in the steam sterilization device 1 can be recovered.

As previously mentioned, the suction pump 4 of the treatment device depicted here is constructed as a diaphragm pump. The diaphragm pump 4 has outlet valves and intake valves 10, 11, which each have a valve disc 12 controlled by the conveying medium. The intake valve 11 of the suction pump 4 is depicted in even greater detail in the FIGS. 3 and 4 in two similar embodiments.

Figure 3:
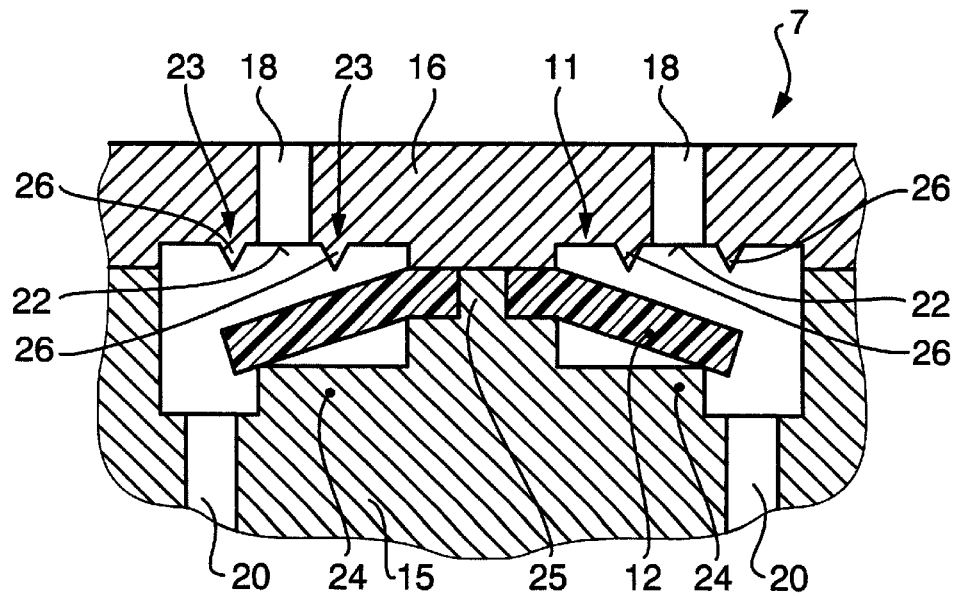
FIG. 3 is the suction pump of the treatment device according to FIG. 1 in a partial cross-section in the area of the intake valve, where the intake valve is depicted in its open position.
Figure 4:
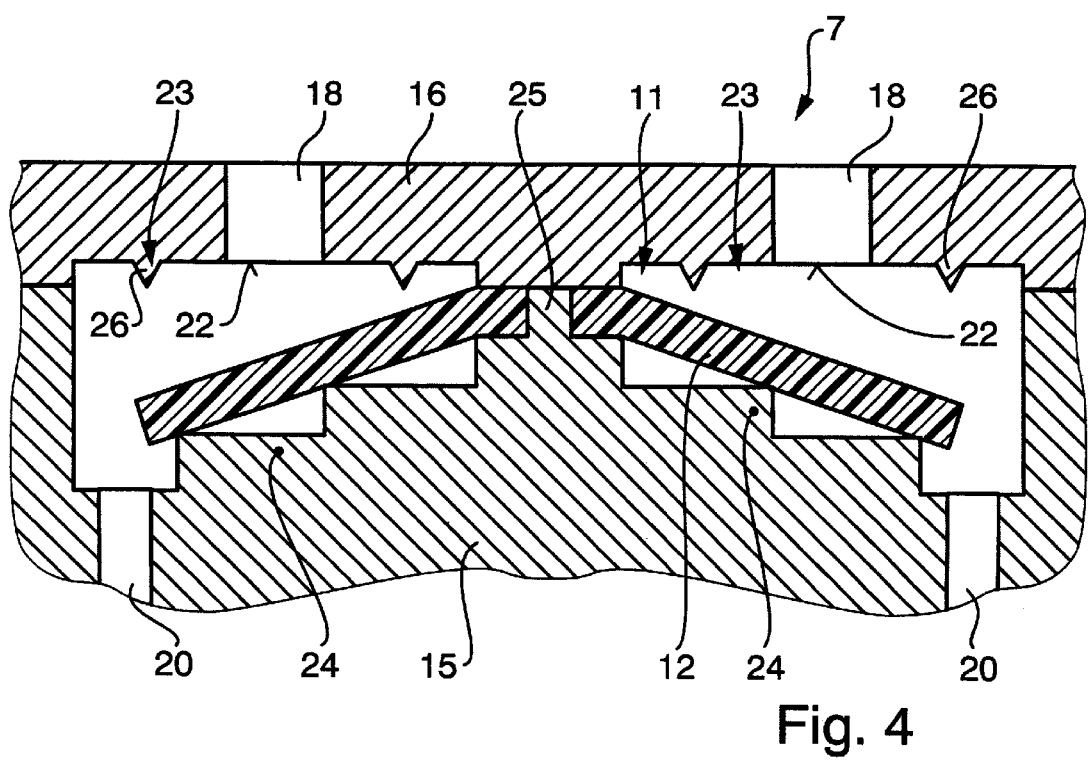
FIG. 4 is a cross-sectional view of an intake valve, similar to FIG. 3, for a treatment device according to FIG. 1.

As is clear from a comparison of FIGS. 1 and 3 to 4, the diaphragm pump 4 has a housing 13, a diaphragm 14, an intermediate cover 15 and a cover plate 16 connected to it. The two covers 15, 16 together form the pump head 7. An outlet channel 17 is isolated in the cover plate 16 as well as an inlet channel 18 connected via the suction line 19 to the treatment and sterilization chamber 2. The valves 10, 11 are connected via the supply lines 20 with the dome shaped pump space 21 in the intermediate cover 15.

In the closed position of the valves 10, 11, each valve disc 12 fits to seal on the valve sealing surface 23 of the pump head that surrounds the valve opening 22. In order to limit the valve opening movement, the valve disc fits in the open position shown in FIGS. 3 and 4 on a rear-side support 24 functioning as a stopper surface. The circular disc shaped valve discs 12 are held centrally by a pin 25 between the cover plate 16 and the intermediate cover 15.

The inherent elasticity of the valve disc material usually provides for a sufficiently fast return of the valve disc 12 into its closing position when the pressure differentials are suitable in the conveying medium in pumping operation. Since with the aid of the cooling device 5 acting on the pump head a re-vaporization of the condensate or condensate film located in the pump space 21 or the valve spaces is prevented, there is the danger when using customary suction pumps that the valve disc 21 even for small liquid quantities of one or two drops, adheres to the sealing surface of the pump head, and that when the absolute pressure is small, small pressure differentials that are present are not sufficient to overcome the adhesion forces and move the valve disc 12.

In order to ensure a flawless operation of the valve discs 12, provided in the intake valve and/or in the outlet valve 11, 10, the sealing contact lines between the sealing side of the valve disc 12 and the valve sealing surface 23 of the pump head 7, which surrounds the at least one valve opening 22, are essentially constructed as lineshaped contact positions. The valve 11 depicted in FIG. 3 and 4 has for this purpose two ring projections 26, which each surround a valve opening 22 on the pump head 7. There, these ring projections 26 have a cross section tapering conically to the contact position.

For the same reason, the contact positions between the rear side of the valve disc 12 and the support 24 for the valve disc 12 located in the open position are constructed here essentially as line-shaped contact positions. The rear-side support 24 of the valves 10, 11 is constructed for this purpose through the edges of a step-shaped projection (see FIG. 3) or several step-shaped projections (see FIG. 4) preferably having line-shaped contact positions. For the valve disc rear side, point-shaped projections could also, however,—not depicted in greater detail here—function as rear-side supports.

Since the valve disc 12 of the valves 10, 11 contacts both the valve sealing surface 23 as well as the rear side support 24 in only a point or linear manner, the adhesion forces acting on the valve disc 12 as a result of a condensate film in the valve spaces, can be kept so small, that the valve disc 12 still oscillates free from disturbance even at small differential pressures between its open position and the closed position. In FIG. 3 and 4 only the intake valve 11 is depicted each time, however, the outlet valve 10 of the treatment or steam sterilization device 1 is correspondingly equipped.

The treatment device depicted here allows a quick and effective pumping out of conveying mediums that are also wet, where the application area of this treatment device is not restricted solely to steam sterilization devices.

Figure 5:
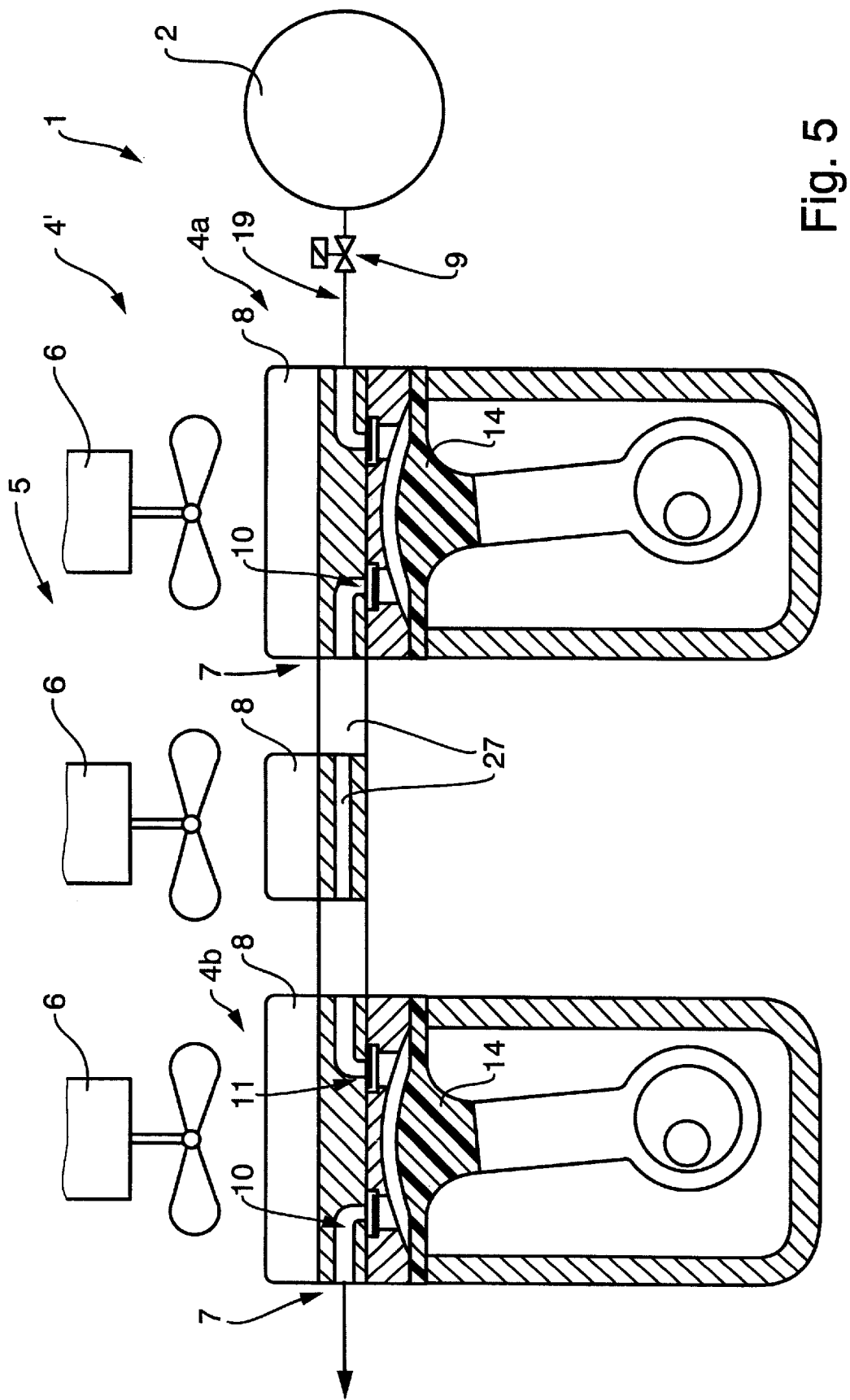
FIG. 5 is a two-stage diaphragm pump shown in a schematic diagram, in which both the two pump stages in the area of their pump heads, as well as the connection channel connecting these adjacent pump stages together, are cooled.

In FIG. 5 a treatment device 1 is depicted which - similar to the device according to FIG. 1—is also constructed as a steam sterilizer. The treatment device 1 according to FIG. 5 has a multi-stage suction pump 4'. The pump stages 4a, 4b are constructed through two diaphragm pumps, one after the other in the flow direction. The outlet of the diaphragm pump that forms the pump stage 4a is connected via a connection channel 27 to the intake of the diaphragm pump provided as a pump stage 4b that follows in the flow direction. In order to rule out a re-vaporization of the conveying medium condensing at the latest in the area of the suction pump 4', a cooling device 5 is provided, which has three cooling fans 6 allocated to each pump stage 4a, 4b and the connection channel 27, respectively. On the pump heads 7 of the pump stages 4a, 4b as well as on the connection channel 27, cooling ribs 8 are provided on the outside which should enlarge the cooling surface and function for the flow conductance of the cooling stream.

In this way, the pump heads 7 of the pump stages 4a, 4b as well as the connection channel 27 connecting them are cooled in such a way that both the head temperature of the pump stages 4a, 4b measured on the pump heads 7 as well as the inner temperature in the connection channel 27 is cooled off below the vaporization or boiling temperature present at the given evacuation pressure.

In a multi-stage suction pump, it is also possible to cool only at least one of the pump heads 7 or only the connection channel 27. However, the embodiment form depicted here is preferred, in which the cooling device 5 has a cooling fan 6 allocated to each of the pump heads 7 and the connectional channel 27. In this it is advantageous when at least one and preferably each of the pump stages has at its outlet and/or at its inlet a valve 10, 11 according to FIGS. 3, 4.

It will be appreciated by those skilled in the art that changes can be made to the embodiments described above without departing from the broad inventive concept thereof. It is understood, therefore, that the invention is not limited to the particular embodiments disclosed, and is intended to cover modifications within the scope and spirit of the present invention.

What is claimed is:

1. A process for evacuating a wet or liquid conveying medium from a treatment chamber (2) of a treatment device (1) using a pumping device (3) having a suction pump (4) with a pump head (7), wherein the conveying medium is cooled off during evacuation along a flow path such that the conveying medium in the pumping device (3) is in or converted to a liquid aggregate state, comprising cooling the conveying medium at least in an area of the pump head (7), such that the pump head (7) is cooled off below a vaporizing or boiling temperature of the conveying medium present at a given evacuation pressure.

2. A process for evacuating a wet or liquid conveying medium from a treatment chamber (2) of a treatment device (1) using a pumping device (3) having a multi-stage suction pump (4, 4') and a connection channel (27) that connects together two pump stages of the multi-stage pump (4, 4') which follow each other in a flow direction, wherein the conveying medium is cooled off during evacuation along a flow path such that the conveying medium in the pumping device (3) is in or converted to a liquid aggregate state, comprising cooling the conveying medium at least in an area of at least one of the connection channel (27) and a pump head (7) of the suction pump (4, 4'), such that the at least one pump head (7) and/or the connection channel (27) is cooled off below a vaporizing or boiling temperature of the conveying medium present at a given evacuation pressure.

3. A device for treatment of an article with a wet or liquid conveying medium, comprising a treatment chamber (2), a pumping device (3) connected to the chamber (2) for evacuation of the conveying medium therefrom, the pumping device (3) comprising a suction pump (4) with a pump head (7), and at least one cooling device (5) for cooling the pumping device (3) at least in a partial area such that the conveying medium in the pumping device (3) is in or converted to the liquid aggregate state, the at least one cooling device being provided for cooling the pump head (7), such that a temperature of the pump head (7) is cooled off below a vaporizing or boiling temperature present at a given evacuation pressure.

4. The device according to claim 3, wherein the at least one cooling device (5) is constructed as an air cooling device.

5. The device according to claim 4, wherein the air cooling device is a fan cooling device.

6. The device according to claim 4, wherein the pump head (7) is arranged in a cooling stream of the air cooling device and has cooling ribs (8) arranged on an outside area thereof to provide an enlarged cooling surface and for flow conductance of the cooling stream.

7. The device according to claim 3, wherein a non-return valve is intermediately connected in a flow path provided between the treatment chamber (2) and an outlet of the pumping device (3).

8. The device according to claim 3, wherein the suction pump (4) is constructed as a single stage diaphragm pump and a non-return valve is provided as an outlet valve (11) of the diaphragm pump.

9. The device according to claim 3, wherein the treatment device (1) is constructed as a steam sterilizer, and the treatment chamber (2) is constructed as a sterilization chamber.

10. A device for treatment of an article with a wet or liquid conveying medium, comprising a treatment chamber (2), a pumping device (3) connected to the chamber (2) for evacuation of the conveying medium therefrom, the pumping device (3) comprising a multi-stage suction pump (4, 4') and a connection channel (27) that connects together two pump stages of the multi-stage pump (4, 4') which follow each other in a flow direction, each stage having a pump head (7), and at least one cooling device (5) for cooling the pumping device (3) at least in a partial area such that the conveying medium in the pumping device (3) is in or converted to the liquid aggregate state, the at least one cooling device being provided for cooling at least one of the pump heads (7) and/or the connection channel (27), such that a temperature of the at least one pump head (7) and/or an inner temperature of the connection channel (27) is cooled off below a vaporizing or boiling temperature present at at given evacuation pressure.

11. The device according to claim 10, wherein the at least one cooling device (5) is constructed as an air cooling device.

12. The device according to claim 11, wherein at least one of the pump heads (7) and the connection channel (27) is arranged in the cooling stream of the air cooling device and has cooling ribs (8) arranged on an outside area to provide an enlarged cooling surface and for flow conductance of the cooling stream.

13. The device according to claim 10, wherein a non-return valve is intermediately connected in a flow path provided between the treatment chamber (2) and an outlet of the pumping device (3).

14. The device according to claim 10, wherein the multi-stage suction pump (4, 4') is constructed as a multi-stage diaphragm pump and a non-return valve is provided as an outlet valve (11) of one of the diaphragm pump stages (4a, 4b).

* * * * *